(12) United States Patent
Dancsi et al.

(10) Patent No.: US 8,314,145 B2
(45) Date of Patent: Nov. 20, 2012

(54) HIGH PURITY 17α-CYANOMETHYL-17β-HYDROXY-ESTRA-4,9-DIENE-3-ONE AND PROCESS FOR THE SYNTHESIS THEREOF

(75) Inventors: Lajosné Dancsi, Budapest (HU); Sándor Mahó, Budapest (HU); Antal Aranyi, Érd (HU); János Horváth, Budapest (HU)

(73) Assignee: Richter Gedeon Vegyeszeti Gyar RT, Budapest (HU)

( * ) Notice: Subject to any disclaimer, the term of this patent is extended or adjusted under 35 U.S.C. 154(b) by 1141 days.

(21) Appl. No.: 12/096,209

(22) PCT Filed: Oct. 11, 2006

(86) PCT No.: PCT/HU2006/000091
§ 371 (c)(1),
(2), (4) Date: Aug. 6, 2008

(87) PCT Pub. No.: WO2007/066158
PCT Pub. Date: Jun. 14, 2007

(65) Prior Publication Data
US 2008/0287404 A1    Nov. 20, 2008

(30) Foreign Application Priority Data
Dec. 5, 2005    (HU) .................................. 05 01132

(51) Int. Cl.
*A61K 31/56*    (2006.01)
*C07J 1/00*    (2006.01)
(52) U.S. Cl. .......... 514/510; 514/710; 560/59; 568/633
(58) Field of Classification Search .................. 552/502; 514/169
See application file for complete search history.

(56) References Cited

U.S. PATENT DOCUMENTS
3,391,165 A    7/1968    Hughes
(Continued)

FOREIGN PATENT DOCUMENTS
EP    0776904    6/1997

OTHER PUBLICATIONS

Prenddin, Rino et al. (HCAPLUS, DN 146:229506 abstract of IT 2001M12663, Industriale Chimica S,r. 1 Italy).*

(Continued)

*Primary Examiner* — Sabiha Qazi
(74) *Attorney, Agent, or Firm* — Jonathan Myers; Andrew Wilford

(57) ABSTRACT

The invention relates to a new process for the synthesis of high purity 17α-cyanomethyl-17β-hydroxy-estra-4,9-diene-3-one (further on dienogest) of formula (I) from 3-methoxy-17-hydroxy-estra-2,5(10)-diene of formula (V). The invention relates also to the high purity 17α-cyanomethyl-17β-hydroxy-estra-4,9-diene-3-one and pharmaceutical compositions containing that as active ingredient. The pharmaceutical compositions according to this invention contain high purity dienogest of formula (I) in which the total amount of impurities is less than 0.1%, while the amount of 4-bromo-dienogest is under the detection limit (0.02%) as active ingredient or at least one of the active ingredients and auxiliary materials, which are commonly used in practice, such as carriers, excipients or diluents. According to our invention the dienogest of formula (I) is synthesized the following way: i) 3-methoxy-17-hydroxy-estra-2,5(10)-diene of formula (V) is reacted with aluminum isopropylate in the presence of cyclohexanone in an inert organic solvent under heating; ii) the so obtained 3-methoxy-estra-2,5(10)-diene-17-one of formula (IV) is reacted with cyanomethyl lithium at a temperature between 0 and −30° C.; iii) the obtained 3-methoxy-17α-cyanomethyl-17β-hydroxy-estra-2,5(10)-diene of formula (III) is reacted with a strong organic acid in tetrahydrofuran solution; iv) the obtained 17α-cyanomethyl-17β-hydroxy-estr-5(10)-ene-3-one of formula (II) is reacted with 1-1.5 equivalent of pyridinium tribromide in pyridine solution at a temperature between 0 and 60° C., then the obtained crude dienogest of formula (I) is purified by recrystallization and preparative HPLC.

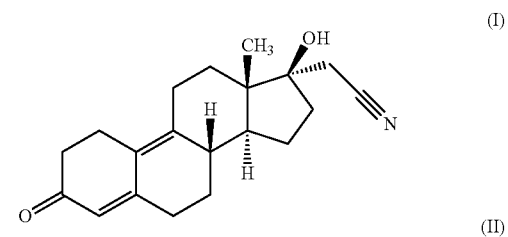

(I)

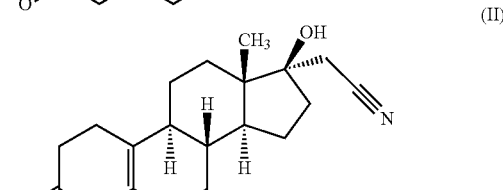

(II)

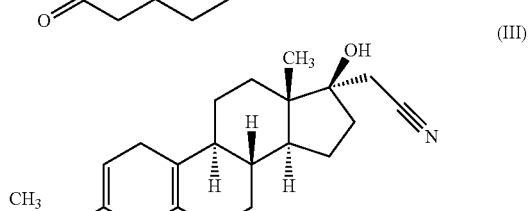

(III)

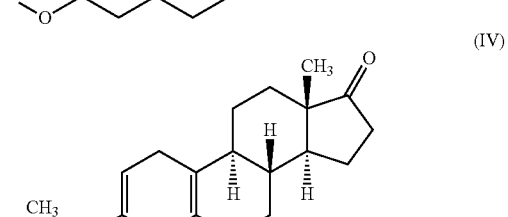

(IV)

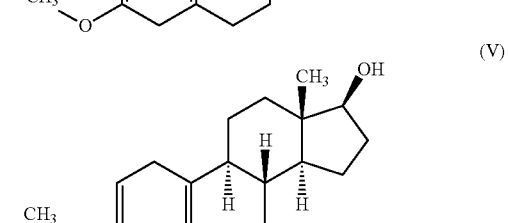

(V)

14 Claims, No Drawings

U.S. PATENT DOCUMENTS 4,248,790 A * 2/1981 Ponsold et al. .................. 552/9
5,438,134 A * 8/1995 Teichmuller et al. ........... 540/32
7,671,045 B2 * 3/2010 Jiang et al. .................... 514/176

OTHER PUBLICATIONS

"Synthesis and Antimalarial Activity of Some Indole and Benzimidazole Amidine Derivatives" Zhang Xjuping et al, and "Synthesis of 17α-Cyanomethyl-17β-Hydroxy-4,9(10)-Diene-3-One and its Derivative of Estra-4,9(10),11(12)-Triene" Cheng Qilu et al, Pharmaceutical industries (1984 (16)9 1.

"Synthesis, Effects, and Metabolism of the Progestagen and Potential Interceptive Dienogest" Kurt Schubert, Natural Products Chemistry 1984.

* cited by examiner

HIGH PURITY 17α-CYANOMETHYL-17β-HYDROXY-ESTRA-4,9-DIENE-3-ONE AND PROCESS FOR THE SYNTHESIS THEREOF

CROSS REFERENCE TO RELATED APPLICATIONS

This application is the US national phase of PCT application PCT/HU2006/000091, filed 11 Oct. 2006, published 14 Jun. 2007 as WO 2007/066158, and claiming the priority of Hungarian patent application PO501132 itself filed 5 Dec. 2005, whose entire disclosures are herewith incorporated by reference.

The invention relates to a new process for the synthesis of; high purity 17α-cyanomethyl-17β-hydroxy-estra-4,9-diene-3-one (further on dienogest) of formula (I)

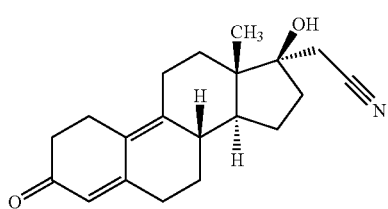

from 3-methoxy-17-hydroxy-estra-2,5(10)-diene of formula (V).

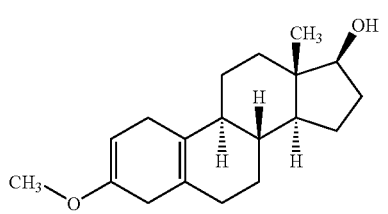

This compound is used as active ingredient in contraceptive pharmaceutical compositions as progestogene component, in the hormone replacement therapy as well as in compositions against endometriosis. The invention relates also to the high purity 17α-cyanomethyl-17β-hydroxy-estra-4,9-diene-3-one and pharmaceutical compositions containing that as active ingredient. The pharmaceutical compositions according to this invention contain high purity dienogest according to this invention as active ingredient or at least one of the active ingredients and auxiliary materials, which are commonly used in practice, such as carriers, excipients or diluents.

In this description high purity dienogest means, that the total amount of impurities is less than 0.1%, while the amount of 4-bromo-dienogest is under the detection limit (0.02%).

Known procedures for the synthesis of diogenest of formula (I) start from intermediates of the total synthesis of estrone. The main difference between the known procedures is that the two double bonds characteristic for the desired compound are already included in the starting material or not, and in the latter case they are formed in the last step of the synthesis.

According to the German patent application DD 132,497 3-methoxy-17β-spiro-1',2'-oxirane-estra-2,5(10)-diene is reacted with an alkali metal cyanide to yield a 17α-cyanomethyl-17β-hydroxy-3-enolether derivative. Then the so obtained compound is hydrolyzed, brominated and dehydrobrominated to furnish the dienogest of formula (I) hi 32% yield. The purity of the obtained dienogest is characterized by the melting point (204-214° C.) and optical rotation ($[\alpha]^{25}_D$=290°, pyridine, c=0.5%). According to the method described in the patent application DD 80,023 3-methoxy-17β-spiro-1',2'-oxirane-estra-2,5(10)-diene used as starting material can be synthesized by reacting dimethylsulfonium methylide and the 17-oxo derivative obtained by Oppenauer oxidation of the 17-hydroxy group of 3-methoxy-17-hydroxy-estra-2,5(10)-diene of formula (V)—latter synthesized by known methods.

The process described in the German patent application DD 160,418 a modification of the above process, in which first the compound of formula (V) is transformed into 3,3-dimethoxy-17-hydroxy-estr-5(10)-ene, the 17 hydroxy group is oxidized with pyridinium chlorocromate—instead of Oppenauer oxidation—then 17β-spiro-1',2'-oxirane is formed with dimethylsulfonium methylide, and the latter is reacted with alkali metal cyanide to obtain 3,3-dimethoxy-17α-cyanomethyl-17β-hydroxy-estr-5(10)-ene. This compound is hydrolyzed with sulfuric acid to give 17α-cyanomethyl-17β-hydroxy-estr-5(10)-ene, from which after bromination and subsequent dehydrobromination the dienogest is obtained in 48% yield. The total yield of the process is 24%.

The German patent application DD 296,495 describes a one-pot synthesis, according to which first the starting ketosteroid—position 3 of which contains a hydroxy or an oxo group protected with one or more alkoxy group—is reacted with cyanomethyl lithium formed in situ in the reaction of lithium alkyls or lithium dialkylamides and acetonitrile in an organic solvent at low temperature. This way a 17-hydroxy and a 17-cyanomethyl group are formed from the 17 oxo group, the obtained reaction mixture is treated with water and the obtained 17-hydroxy-17-cyanomethyl derivative is isolated or transformed into dienogest by direct acidic hydrolysis. The yield of the final product is 82% starting from 3,3-dimethoxy-estra-5(10),9(11)-diene-17-one, while using the 3,3-(1,3-propylenedioxi)-estra-5(10),9(11)-diene derivative as starting material the yield is 80%. The purity of the product is characterized by the melting point: 208-211.5 ° C. The synthesis consist of 6 steps included the preparation of the 17-oxo derivative used as starting material.

According to the patent application EP 0776904 3,3-(2,2-dimethylpropylene-1,3-dioxy)-4,5-seco-estr-9-ene-5,17-dione is transformed first to estra-4,9-diene-3,17-dione and the latter to 3,3-ethylenedioxy-estra-5(10),9(11)-diene-17-one. After reacting with dimethylsulfonium iodide a 17p-spiro-1',2'-oxirane derivative is obtained which is reacted with potassium cyanide to give 17α-cyanomethyl-17β-hydroxy-estra-5(10),9(11)-diene-3-ethyleneketal. The ketal group of this compound is hydrolyzed with hydrochloric acid to give the final product dienogest in >98% purity.

According to the processes starting from the above mentioned 3-methoxy-17-hydroxy-estra-2,5(10)-diene of formula (V) first a 3,3-dialkoxy-ketal-5(10)-ene derivative is formed, then the latter is oxidized to a keto compound, which is reacted with dimethylsulfonium-methylide to give a 17β-spiro-1',2'-oxirane derivative, and this is transformed into 17α-cyanomethyl-17β-hydroxy derivative. The obtained compound is hydrolyzed with acid, then brominated and dehydrobrominated to yield the dienogest of formula (I) in 6 steps.

According to the other process starting also from compound of formula (V) after the oxidation of the hydroxyl group in position 17 by Oppenauer oxidation the 17β-spiro-1',2'-oxirane derivative is synthesized, which is reacted with alkali metal cyanide, the obtained. 3-enolether is hydrolyzed, brominated and dehydrobrominated to yield dienogest in 5 steps.

According to the other method mentioned above 3,3-ethylenedioxy-estra-5(10),9(11)-diene-17-one is either reacted directly with cyanomethyl lithium or spiro-oxirane is formed first and the oxirane ring is opened with alkali cyanide to give the 17α-cyanomethyl-17β-hydroxy derivative, which is hydrolyzed to yield the final product of formula (I).

The syntheses of the 17β-spiro-1',2'-oxirane derivatives starting from 17-keto compounds and dimethylsulfonium derivatives according to the methods described in patent, applications DD 132,497 and EP 0,776,904 are expensive and environmentally not friendly. The use of alkali cyanide for the opening of the oxirane ring requires keeping to strict safety instructions and after the work-up of the reaction mixture causes environmental problems.

In the above mentioned patent applications the quality of the product is characterized only by melting point or at most substance content. The requirements of recent pharmacopoeia specify several other method of examination for the amount of substance and impurities, such as thin layer and liquid chromatography, as well as determine and limit the amount and the number of impurities.

Our aim was to eliminate the above mentioned disadvantages of the known procedures and elaborate a shorter, more economical and environmentally friendly synthesis, which can be carried out on industrial scale preferably using an intermediate of the estrone total synthesis, the 3-methoxy-17-hydroxy-estra-2,5(10)-diene of formula (V) as starting material.

Our other aim was to synthesize a high purity product, in which the total amount of impurities is less than 0.1%, while the amount of 4-bromo-dienogest is under the detection limit (0.02%), therefore it is suitable for producing different formulations of drugs.

Surprisingly it was found, that using the compound of formula (V) as starting material in the synthesis of compound of formula (III) it is not necessary to form the 17β-oxirane derivative, followed by opening the epoxide ring with alkali cyanide, as well as it is not required to synthesize the 3,3-dialkoxy-ketal from the enolether group of compound of formula (V) and oxidize the hydroxyl group in position 17 with pyridinium chlorocromate. Using the reaction conditions according to our invention the compound of formula (V) can be oxidized by Oppenauer oxidation in good yield (90%) without damaging the A-ring (aromatization). This way we could elaborate a 4-step synthesis, which is shorter than the known procedures.

According to our invention the dienogest of formula (I) is synthesized the following way:

i) 3-methoxy-17-hydroxy-estra-2,5(10)-diene of formula (V) is reacted with aluminum isopropylate in the presence of cyclohexanone in an inert organic solvent under heating ii) the so obtained 3-methoxy-estra-2,5(10)-diene-17-one of formula (IV)

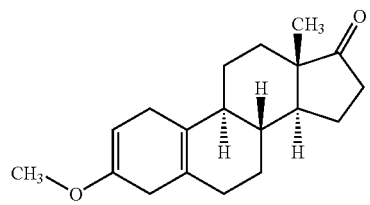

is reacted with cyanomethyl lithium at a temperature between 0 and −30° C., iii) the obtained 3-methoxy-17α-cyanomethyl-17β-hydroxy-estra-2,5(10)-diene of formula (III)

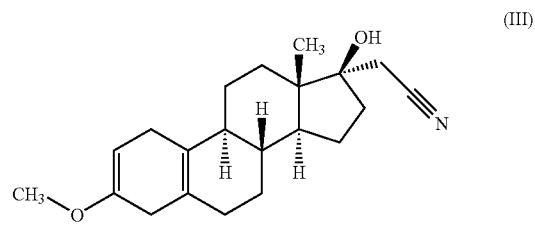

is reacted with a strong organic acid in tetrahydrofuran solution, iv) the obtained 17α-cyanomethyl-17β-hydroxy-estr-5(10)-ene-3-one of formula (II)

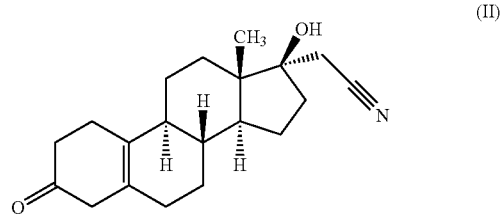

is reacted with 1-1.5 equivalent of pyridinium tribromide in pyridine solution at a temperature between 0 and 60° C., then the obtained crude dienogest of formula (I) is purified by recrystallization and preparative HPLC.

Step ii) is preferably carried out at a temperature between −10 and −20° C., while step iv) between 25 and 50° C. using 1.05 equivalent of pyridinium tribromide.

Recrystallization is preferably carried out using acetone, ethyl acetate, acetonitrile, methanol, ethanol, or aqueous mixtures of different ratio of these solvents, as well as mixtures of different ratio of dichloromethane and diisopropyl ether or isopropanol or tert-butyl methyl ether.

In order to obtain high purity the so obtained recrystallized product is further purified by preparative HPLC using silica gel as adsorbent and different solvent systems as eluents, such as dichloromethane/ethyl acetate, dichloromethane/tert-butyl methyl ether, or dichloromethane/acetone. Dichloromethane is evaporated from the eluate and the obtained high purity dienogest is isolated from the -other component of the used solvent system, e.g. ethyl acetate, tert-butyl methyl ether, acetone, or diisopropyl ether, methanol, ethanol or aqueous mixtures of different ratio of these solvents.

Advantages of our process are as follows:
the synthesis can be carried out on industrial scale, increasing the batch size compared to the size described in the Examples do not cause technical problems and do not influence the purity of the final product the starting material of the synthesis, the 3-methoxy-17-hydroxy-estra-2,5(10)-diene of formula (V), is an easily accessible industrial product, the synthesis consist of less reaction steps—only 4—than the processes known from the literature—5-6-8 steps, using the reaction conditions according to our invention the yields of the reaction, steps of the synthesis are much higher, than yields given in the prior arts. The yield of every step is higher than 80%, therefore the total yield is over 50%.

the quality of the synthesized high purity dienogest is better, than the quality requirements of the pharmacopoeia. The amount of impurities is determined by, HPLC. According to these measurements in our product the total amount of impurities is less than 0.1% and the amount of 4-bromo-dienogest, which is an impurity detectable in the marketed pharmaceutical compositions in more than 0.1%, is under the detection limit (0.02%).

In the cyanomethylation reaction alkali cyanides and dimethylsulfonium derivatives are not used in accordance with environmental regulations and economic considerations, as well as expensive and hazardous butyl lithium is not used either—a hexane solution of hexyllithium is used instead of them.

The process according to our invention is illustrated by the following not limiting examples.

EXAMPLE 1

3-Methoxy-estra-2,5(10)-diene-17-one

To a stirred solution of 106.3 g (0.52 mmol) of aluminum isopropoxide in 2000 ml of dry toluene 720 ml of cyclohexanone, 0.35 g of 2,6-ditert-butyl-4-methyl-phenol and 100 g (0.307 mol) 3-methoxy-17-hydroxy-estra-2,5(10)-diene were added, then the reaction mixture was stirred at 108-110° C. for 1 h. The reaction was followed by TLC. After completion of the reaction the mixture was cooled to 20-25° C., 200 ml of water was added and the so obtained mixture was stirred for 1 h. The precipitated aluminum hydroxide was filtered off and the filtrate was concentrated to a volume of 250 ml under reduced pressure. A mixture of 200 ml of methanol and 100 ml of water was added to this concentrated warm—about 60° C.—solution, the obtained suspension was cooled to 20-25° C. and stirred for 1 h. The precipitated crystalline product was filtered off and dried below 40° C. in vacuum to yield 76.4 g (87%) of the title compound.

Purity: min. 98% (HPLC)
Melting point: 106-110° C.

EXAMPLE 2

3-Methoxy-17α-cyanomethyl-17β-hydroxy-estra-2,5(10)-diene 410 ml (1.012 mol) of 2.5 M hexyllithium solution was diluted with 300 ml of dry tetrahydrofuran, the solution was cooled to −20° C. and 58 ml (1.112 mol) of acetonitrile was added. To the so obtained suspension of cyanomethyl lithium a solution of 144.8 g (0.506 mol) of 3-methoxy-estra-2,5(10)-diene-17-one in 1450 ml of tetrahydrofuran was added between −20 and −10° C. and the reaction mixture was stirred between −20 and −10° C. until completion of the reaction—followed by TLC. After completion of the reaction 640 ml of water was added, the organic phase was separated, washed twice with 60 ml of water, and concentrated to a volume of 720 ml under reduced pressure. The concentrated solution was cooled to 20-25° C., 720 ml of water was added, the precipitated crystalline product was filtered off and dried below 40° C. in vacuum. The obtained crude product was recrystallized from ethanol to yield 143.4 g (86.5%) of the title compound.

Purity: min. 98% (HPLC)
Melting point: 145-150° C.

EXAMPLE 3

17α-Cyanomethyl-17β-hydroxy-estr-5(10)-ene-3-one

To a stirred solution of 100.8 g (0.8 mol) of oxalic acid dihydrate in 560 ml of water a solution of 131 g (0.4 mol) of 17α-cyanomethyl-17β-hydroxy-3-methoxy-estra-2,5(10)-diene in 1050 ml of tetrahydrofuran was added with cooling. After stirring at 20-25° C. for 1 h the precipitated product was filtered off and dried below 50° C. in vacuum. The obtained crude product was recrystallized from ethyl acetate to yield 107 g (85.6%) of the title compound.

Purity: min. 98% (HPLC)
Melting point: 170-175° C.

EXAMPLE 4

17α-Cyanomethyl-17β-hydroxy-estra-4,9-diene-3-one (crude dieno est)

A stirred solution of 142 g (0.45 mol) of 17α-cyanomethyl-17β-hydroxy-estr-5(10)-ene-3-one in 850 ml of pyridine was cooled to 20-25° C. and a solution of 150 g (0.47 mol) of pyridinium tribromide in 640 ml of pyridine was added while the temperature of the reaction mixture was allowed to rise to 50° C. After stirring for 1 h the reaction mixture was added to a stirred mixture of 320 ml of concentrated sulfuric acid and 5600 ml of water. The precipitated crystals were filtered off and dried below 60° C. in vacuum. The obtained crude product was recrystallized from acetone to yield 116 g (83%) of the title compound.

Amount of active ingredient: min. 97% (HPLC).
4-Bromo-dienogest impurity: max. 1% (HPLC).
Melting point: 210-213° C.
$[\alpha]^{20}_D = -318°$ (c=1%, dichloromethane).

EXAMPLE 5

Purification of Dienogest by Preparative HPLC

A dynamic axial compression metal column (diameter: 5 cm; length: 60 cm) was filled with 510 g silica gel (Uetikon C-gel C-490, particle size: 15-35 μm) suspended in 1400 ml of dichloromethane and the column was conditioned with a 70:30 mixture of dichloromethane/ethyl acetate eluent (2500 ml). A solution of 8.5 g of crude dienogest in 210 ml of dichloromethane was injected to the column and the above mentioned solvent system was used as eluent with a flow rate of 85 ml/min. UV detector was used for detection. The fractions containing the pure compound (3600 ml) were concentrated, ethyl acetate was distilled off from the residue and the obtained dienogest was recrystallized from ethyl acetate to yield after drying below 60° C. in vacuum 7.53 g (90.6%) of pure dienogest.

Total amount of impurities: maximum 0.1% (HPLC).
Individual impurities: maximum 0.02% (HPLC).

Melting point: 211-214° C.

$[\alpha]^{20}_D = -322°$ (c=1%, dichloromethane).

EXAMPLE 6

Purification of Dienogest by Preparative HPLC

A glass column (diameter: 2.6 cm; length: 46 cm) was filled with 120 g silica gel (Uetikon C-gel C-490, particle size: 15-35 μm) and the column was conditioned with a 90:10 mixture of dichloromethane/acetone eluent. A solution of 2 g of crude dienogest in 50 ml of dichloromethane was injected to the column and the above mentioned solvent system was used as eluent with a flow rate of 10 ml/min. UV detector was used for detection. The fractions containing the pure compound (700 ml) were concentrated, acetone was distilled off from the residue and the obtained dienogest was recrystallized from acetone to yield after drying below 60° C. in vacuum 1.77 g (88.5%) of pure dienogest.

Total amount of impurities: maximum 0.1% (HPLC).

Individual impurities: maximum 0.02% (HPLC).

Melting point: 211-214° C.

$[\alpha]^{20}_D = -322°$ (c=1%, dichloromethane).

EXAMPLE 7

Purification of Dienomest by Preparative HPLC

A glass column (diameter: 2.6 cm; length: 46 cm) was filled with 120 g silica gel (Uetikon C-gel C-490, particle size: 15-35 pm) and the column was conditioned with a 90:10 mixture of dichloromethane/acetone eluent. A solution of 2 g of crude dienogest in 50 ml of dichloromethane was injected to the column and the above mentioned solvent system was used as eluent with a flow rate of 10 ml/min. UV detector was used for detection. The fractions containing the pure compound (700 ml) were concentrated, acetone was distilled off from the residue and the obtained dienogest was recrystallized from acetone to yield after drying below 60° C. in vacuum 1.77 g (88.5%) of pure dienogest.

Total amount of impurities: maximum 0.1% (HPLC).

Individual impurities: maximum 0.02% (HPLC).

Melting point: 211-214° C.

$[\alpha]^{20}_D = -322°$ (c=1%, dichloromethane).

What we claim is:

1. A process for the synthesis of 17α-cyanomethyl-17β-hydroxy-estra-4,9-diene-3-one of the Formula (I)

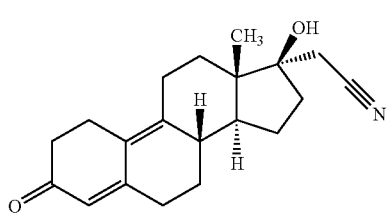

which comprises the steps of:
(i) oxidizing 3-methoxy-17-hydroxy-estra-2,5(10)-diene of Formula (V)

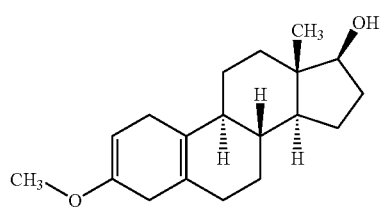

with aluminum isopropylate in the presence of cyclohexanone in an inert organic solvent under heating to obtain a compound of the Formula (IV)

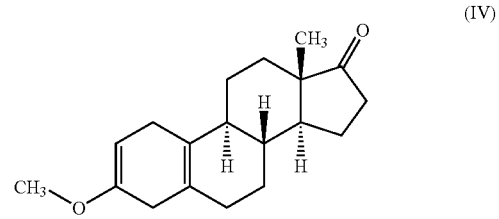

(ii) cyanomethylating the compound of the Formula (IV) with cyanomethyl lithium, wherein the cyanomethyl lithium reagent is prepared in situ from hexyllithium and acetonitrile, at a temperature between 0 and −30° C., to obtain 3-methoxy-17α-cyanomethyl-17β-hydroxy-estra-2,5(10)-diene of Formula (III)

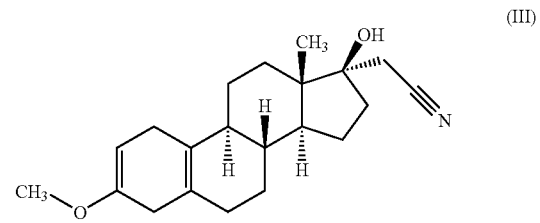

(iii) acidifying the compound of the Formula (III) with a strong organic acid in tetrahydrofuran solution to obtain 17α-cyanomethyl-17β-hydroxy-estr-5(10)-ene-3-one of Formula (II)

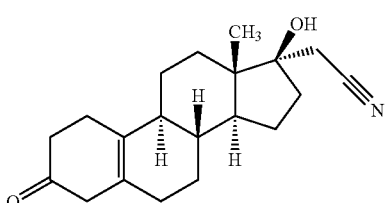

and (iv) reacting the compound of the Formula (II) with 1-1.5 equivalent of pyridinium tribromide in pyridine solution at a temperature between 0 and 60° C., to obtain the compound of the Formula (I); and optionally purifying the obtained crude compound of the Formula (I).

2. The process defined in claim 1 wherein according to step (i), the oxidation is carried out in toluene in the presence of 20 to 25 equivalents of cyclohexanone at a temperature between 100 and 120° C.

3. The process defined in claim 1, wherein according to step (ii) the cyanomethyl lithium reagent is prepared in situ from hexyllithium and acetonitrile.

4. The process defined in claim 1 wherein according to step (ii) the cyanomethylation reaction is carried out at a temperature between −10 and −20° C.

5. The process defined in claim 1 wherein according to step (ii), 2 equivalents of cyanomethyl lithium reagent are used per equivalent of the compound of the Formula (IV).

6. The process defined in claim 1 wherein according to step (iii) the acidic treatment is carried out with a di- or tribasic organic acid in tetrahydrofuran.

7. The process defined in claim 1 wherein according to step (iii) the acidic treatment is carried out with 2 equivalents of oxalic acid dihydrate.

8. The process defined in claim 1 wherein according to step (iv) the compound of Formula (II) is reacted with 1.05 equivalent of pyridinium tribromide.

9. The process defined in claim 1 wherein according to step (iv) the compound of Formula (II) is reacted with pyridinium tribromide at a temperature between 0 and 60° C.

10. The process defined in claim 1 wherein according to step (iv) the compound of Formula (II) reacts with pyridinium tribromide between 25 and 50° C.

11. The process defined in claim 1, wherein following step (iv), the compound of the Formula (I) is purified by HPLC using silica gel as adsorbent.

12. The process defined in claim 11, wherein the compound of the Formula (I) is purified by HPLC using the following solvent mixtures as eluents: 70:30 dichloromethane/ethyl acetate or 80:20 dichloromethane/tert-butyl methyl ether or 90:10 dichloromethane/acetone.

13. The process defined in claim 11, further comprising the step of:
    recrystallizing the compound of the Formula (I), purified by preparative HPLC, using ethyl acetate, acetone, tert-butyl methyl ether, diisopropyl ether, acetonitrile, methanol, ethanol or aqueous mixtures of different ratio of these solvents for the recrystallization.

14. A process for the synthesis of 17α-cyanomethyl-17β-hydroxy-estra-4,9-diene-3-one of the Formula (I)

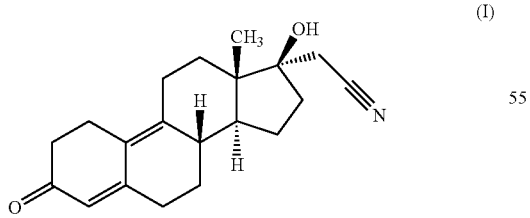

which comprises the steps of:
(i) oxidizing 3-methoxy-17-hydroxy-estra-2,5(10)-diene of formula (V)

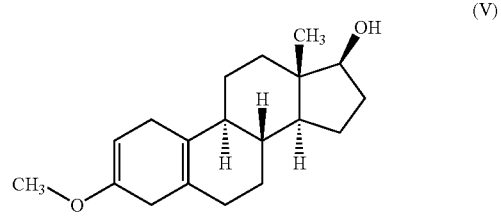

with aluminum isopropylate in the presence of cyclohexanone in toluene as an inert organic solvent under heating to a temperature of 100 to 120° C. to obtain a compound of the Formula (IV)

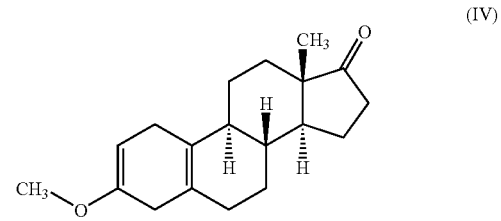

(ii) cyanomethylating the compound of the Formula (IV) with cyanomethyl lithium at a temperature between −10° C. and −30° C., to obtain 3-methoxy-17α-cyanomethyl-17β-hydroxy-estra-2,5(10)-diene of Formula (III)

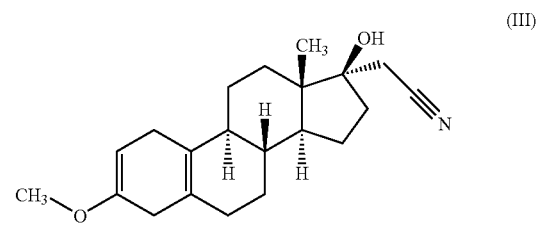

(iii) acidifying the compound of the Formula (III) with oxalic acid dihydrate in tetrahydrofuran solution to obtain 17α-cyanomethyl-17β-hydroxy-estr-5(10)-ene-3-one of Formula (II)

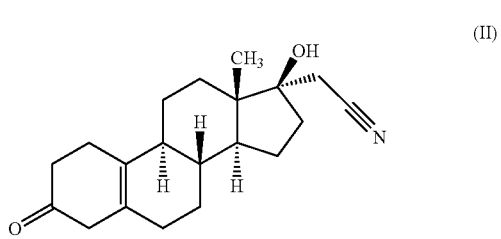

and
(iv) reacting the compound of the Formula (II) with 1-1.5 equivalent of pyridinium tribromide in pyridine solution at a temperature between 0 and 60° C., to obtain the compound of the Formula (I); and optionally purifying the obtained crude compound of the formula (I).

* * * * *